(12) United States Patent
Seo et al.

(10) Patent No.: US 10,758,564 B2
(45) Date of Patent: Sep. 1, 2020

(54) METHOD FOR SYNTHESIZING HIGH-PURITY MONTMORILLONITE

(71) Applicant: KOREA INSTITUTE OF GEOSCIENCE AND MINERAL RESOURCES, Daejeon (KR)

(72) Inventors: Sung Man Seo, Pohang-si (KR); Il Mo Kang, Seoul (KR); Ki Min Roh, Daejeon (KR); Dae Young Kim, Geumsan-gun (KR); Jae Hwan Kim, Pohang-si (KR)

(73) Assignee: KOREA INSTITUTE OF GEOSCIENCE AND MINERAL RESOURCES, Daejeon (KR)

( * ) Notice: Subject to any disclaimer, the term of this patent is extended or adjusted under 35 U.S.C. 154(b) by 0 days.

(21) Appl. No.: 16/158,390

(22) Filed: Oct. 12, 2018

(65) Prior Publication Data

US 2019/0111076 A1  Apr. 18, 2019

(30) Foreign Application Priority Data

Oct. 12, 2017  (KR) ........................ 10-2017-0132137

(51) Int. Cl.
*A61K 8/26* (2006.01)
*A61K 33/06* (2006.01)
*A61Q 19/00* (2006.01)
*C01B 33/26* (2006.01)
*C01B 33/40* (2006.01)

(52) U.S. Cl.
CPC ............ *A61K 33/06* (2013.01); *A61K 8/26* (2013.01); *A61Q 19/00* (2013.01); *C01B 33/26* (2013.01); *C01B 33/40* (2013.01); *B01J 2208/00017* (2013.01)

(58) Field of Classification Search
CPC .. A61K 33/06; B01J 2208/0007; C01B 33/26; C01B 33/40
See application file for complete search history.

(56) References Cited

U.S. PATENT DOCUMENTS

| 3,310,373 | A | * | 3/1967 | Johnson | .............. | C01B 33/2807 |
| | | | | | | 423/711 |
| 3,671,190 | A | * | 6/1972 | Neumann | .............. | C01B 33/405 |
| | | | | | | 423/331 |
| 4,056,146 | A | * | 11/1977 | Hall | ........................ | C09K 8/72 |
| | | | | | | 166/300 |

(Continued)

FOREIGN PATENT DOCUMENTS

| CN | 103418373 | * | 12/2013 | .............. B01J 23/44 |
| CN | 105289542 | * | 2/2016 | .............. B01J 20/26 |

(Continued)

OTHER PUBLICATIONS

Machine translation of JP2014114185, publication date Jun. 26, 2014.*

*Primary Examiner* — Jun Li
(74) *Attorney, Agent, or Firm* — Lex IP Meister, PLLC

(57) ABSTRACT

A method for synthesizing high purity montmorillonite is disclosed. According to this synthesis method, bentonite is dissolved in aqua regia to produce a solution and then sodium hydroxide (NaOH) is added to the solution to produce a mixed solution. Then, the mixed solution is kept in a sealed state at a temperature of 90° C. inclusive to 100° C. exclusive to synthesize montmorillonite crystals.

4 Claims, 5 Drawing Sheets

(56) References Cited

U.S. PATENT DOCUMENTS

| | | | | |
|---|---|---|---|---|
| 6,099,820 A | * | 8/2000 | Miller | C01B 39/46 |
| | | | | 423/700 |
| 2008/0064591 A1 | * | 3/2008 | Siler | B01J 29/89 |
| | | | | 502/242 |
| 2010/0081566 A1 | * | 4/2010 | Sanchez-Valente | ................ |
| | | | | B01J 35/002 |
| | | | | 502/73 |

FOREIGN PATENT DOCUMENTS

| JP | 2014-114185 | 6/2014 |
|---|---|---|
| KR | 10-1992-0009695 | 6/1992 |

\* cited by examiner

[FIG. 1]
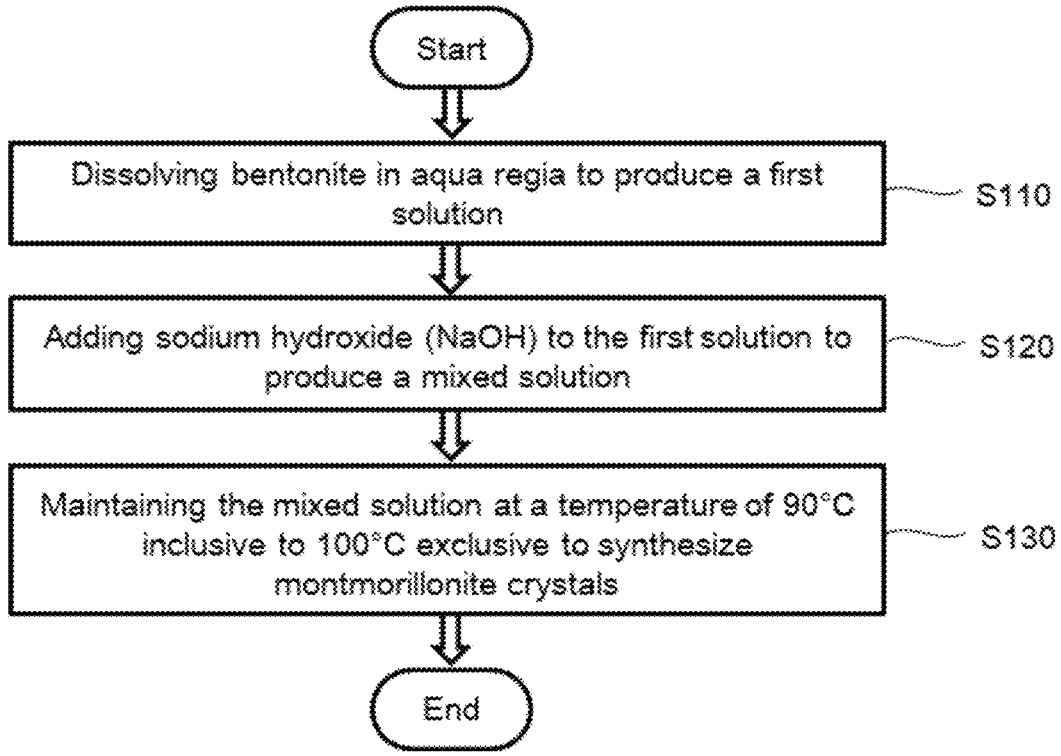
[FIG. 2]
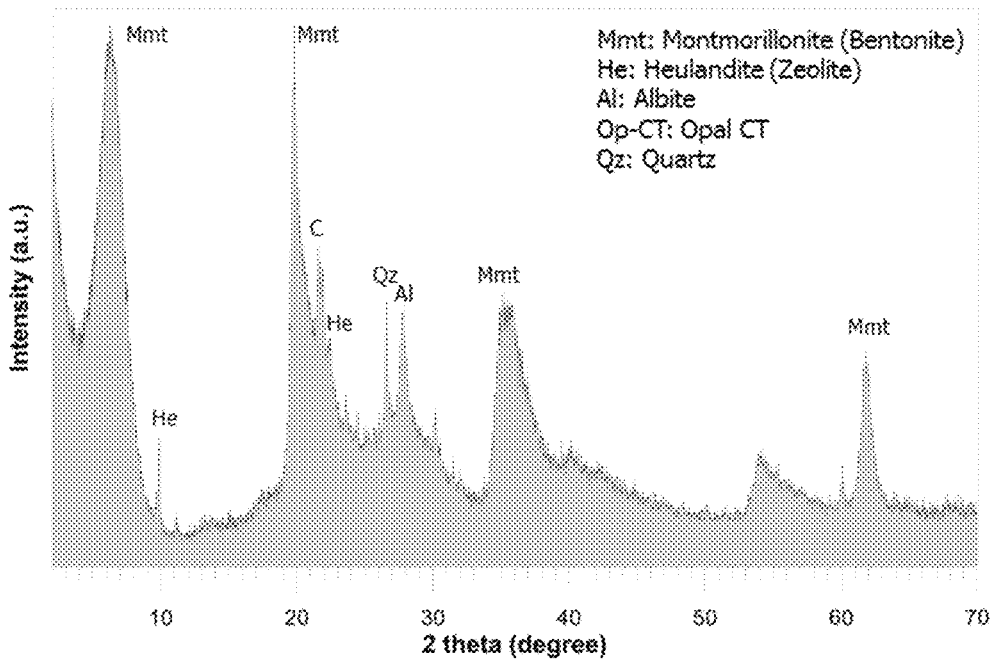

[FIG. 3]
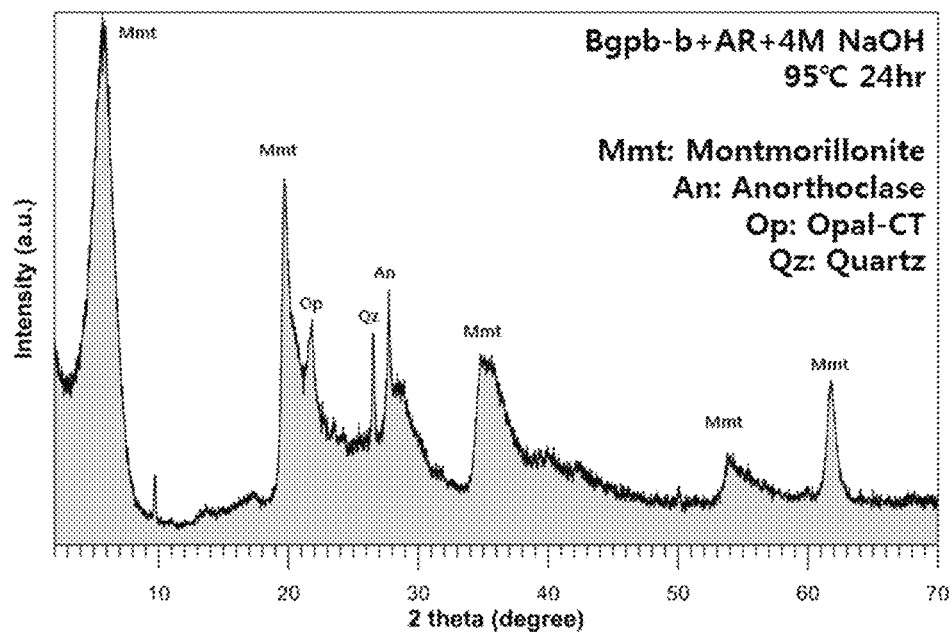
[FIG. 4]
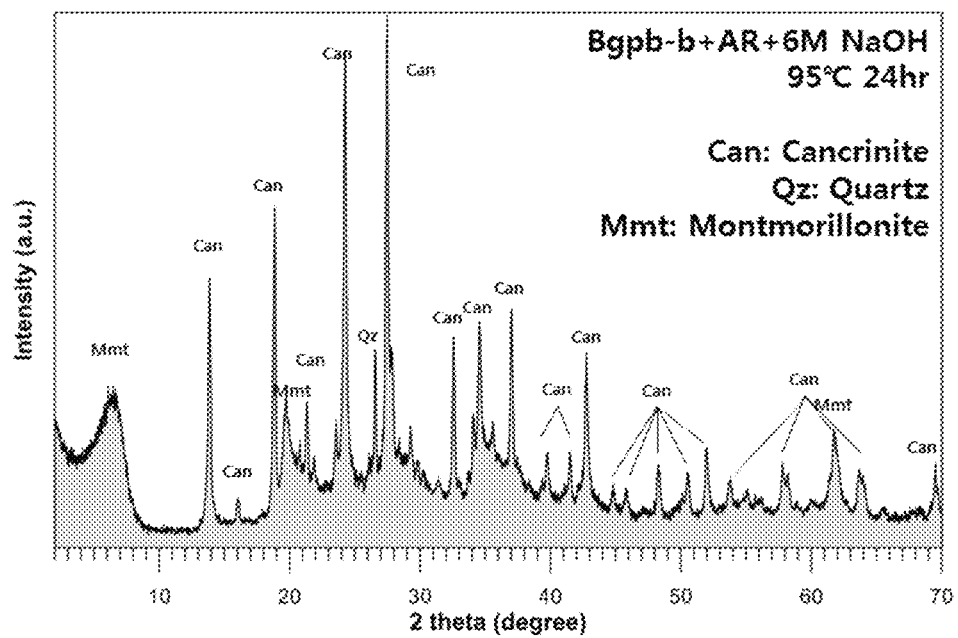

[FIG. 5]
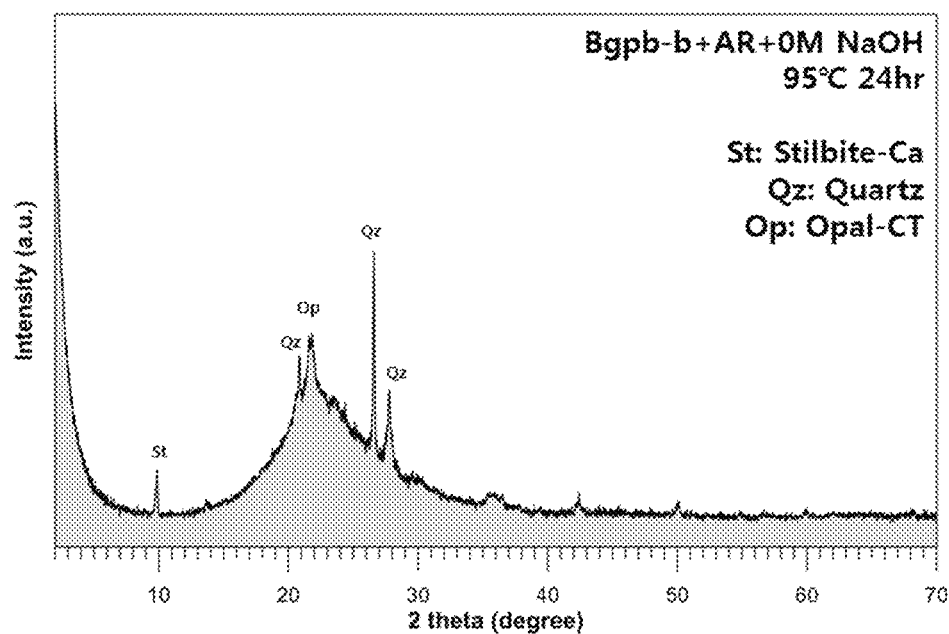
[FIG. 6]
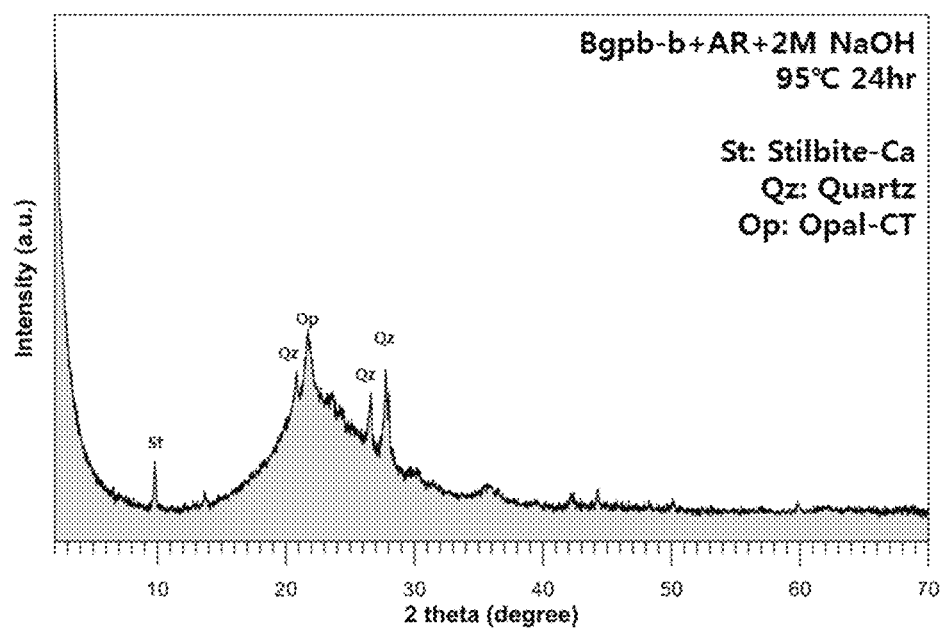

[FIG. 7]
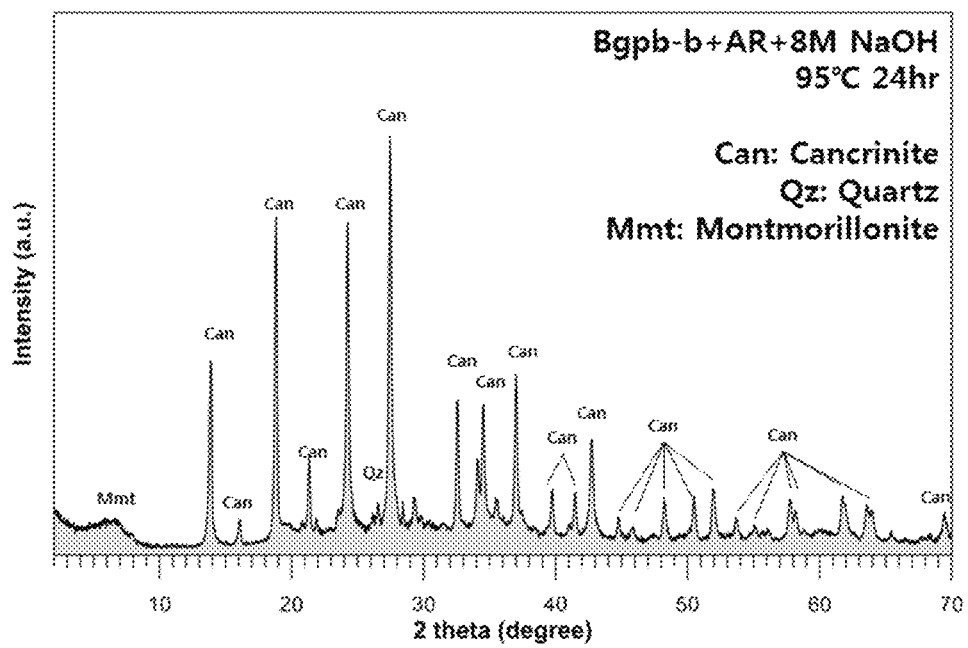
[FIG. 8]
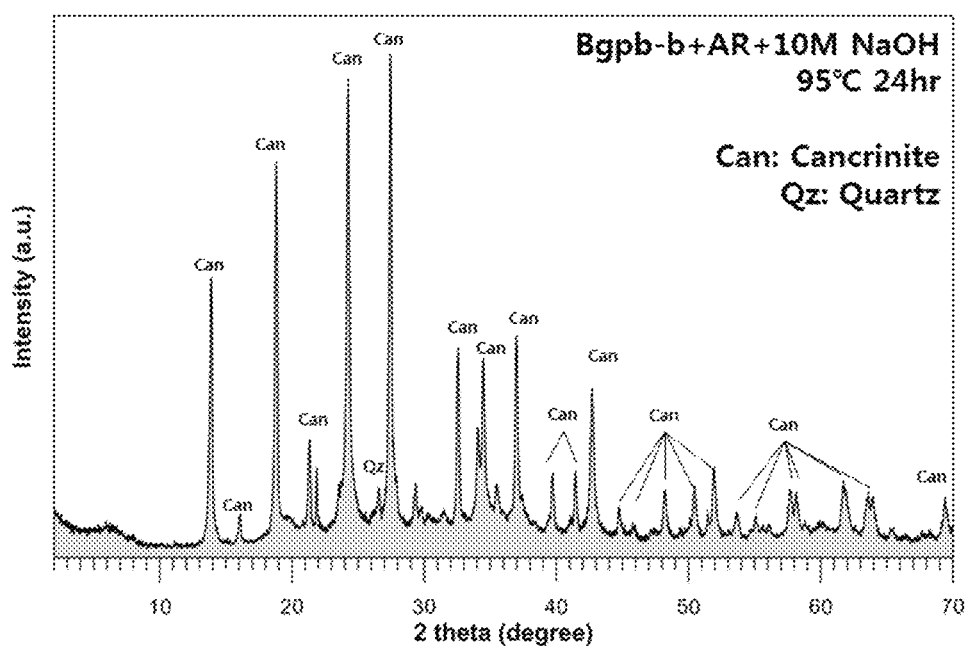

[FIG. 9]
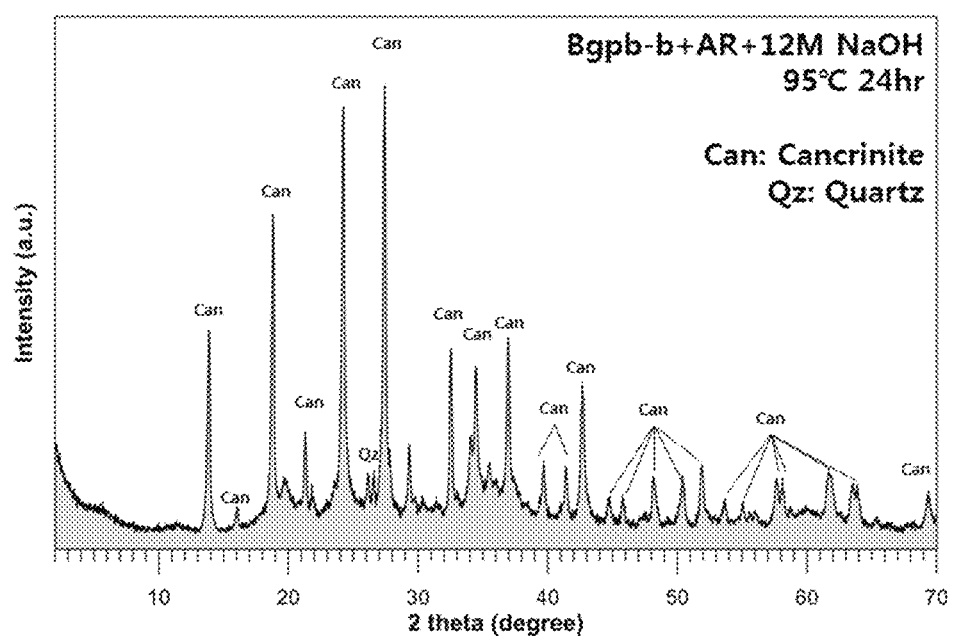

METHOD FOR SYNTHESIZING HIGH-PURITY MONTMORILLONITE

CROSS-REFERENCE TO RELATED APPLICATION

This application is based on and claims the benefit of priority to Korean Patent Application No. 10-2017-0132137, filed on Oct. 12, 2017, in the Korean Intellectual Property Office, the disclosure of which is incorporated herein in its entirety by reference.

TECHNICAL FIELD

The present disclosure relates to a hydrothermal synthesis of montmorillonite used as a source material for pharmaceuticals or cosmetics.

BACKGROUND

High-purity smectite-based montmorillonite is widely used as a raw material for medicines and cosmetics. In order to synthesize such high-purity montmorillonite, conventional high-temperature and high-pressure hydrothermal synthesis was mainly used.

However, the synthesis of the high purity montmorillonite using the conventional high-temperature and high-pressure hydrothermal synthesis increases the manufacturing cost.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

The purpose of the present disclosure is to provide a method for synthesizing high purity montmorillonite by low-temperature hydrothermal synthesis using natural bentonite as starting material.

In one aspect of the present disclosure, there is provided a method for synthesizing montmorillonite, the method comprising: dissolving bentonite in aqua regia to produce a first solution; adding sodium hydroxide (NaOH) to the first solution to produce a mixed solution; and maintaining the mixed solution at a temperature of 90° C. inclusive to 100° C. exclusive to synthesize montmorillonite crystals.

In one embodiment, the bentonite includes finely-pulverized particles made of natural bentonite, each particle having a size of 2 mm or smaller.

In one embodiment, the aqua regia includes a mixture of hydrochloric acid (HCl) and nitric acid (HNO3) at a molar ratio of about 1:3.

In one embodiment, adding the sodium hydroxide (NaOH) to the first solution includes adding to the first solution a sodium hydroxide aqueous solution having a concentration of 3 M to 7 M.

In one embodiment, the sodium hydroxide aqueous solution is added to the first solution so that pH of the mixed solution is in a range of 11 to 13.

In one embodiment, maintaining the mixed solution includes maintaining the mixed solution in a sealed state for about 20 to 30 hours.

In one embodiment, the synthesized montmorillonite crystals have a specific surface area of about 125 to 135 $cm_2/g$.

According to the present disclosure, the relatively low-temperature hydrothermal synthesis using the readily available natural bentonite as a starting material may allow synthesizing montmorillonite with high purity and high specific surface area.

BRIEF DESCRIPTION OF THE DRAWINGS

FIG. 1 is a flow chart illustrating a method for synthesizing high purity montmorillonite according to an embodiment of the present disclosure.

FIG. 2 is an X-ray diffraction pattern measured for calcium-type bentonite taken from Gampo40 mine (located in South Korea) as a starting material.

FIG. 3 to FIG. 9 are X-ray diffraction patterns measured for materials synthesized according to the present examples 1 and 2 and comparative examples 1 to 5.

DETAILED DESCRIPTIONS

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following description, numerous specific details are set forth in order to provide a thorough understanding of the present disclosure. The present disclosure may be practiced without some or all of these specific details. In other instances, well-known process structures and/or processes have not been described in detail in order not to unnecessarily obscure the present disclosure.

As used herein, the term "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure."

FIG. 1 is a flow chart illustrating a method for synthesizing high purity montmorillonite according to an embodiment of the present disclosure.

Referring to FIG. 1, a method for synthesizing high purity montmorillonite according to an embodiment of the present disclosure may include a first step for dissolving bentonite in aqua regia to produce a first solution (S110); a second step for adding sodium hydroxide (NaOH) to the first solution to produce a mixed solution (S120); and a third step for maintaining the mixed solution at a temperature of 90° C. inclusive to 100° C. exclusive to synthesize montmorillonite crystals (S130). The method can produce dioctahedral smectite-based pure montmorillonite using natural bentonite.

In the first step (S110), the bentonite may be natural bentonite-based mineral particulates. For example, natural bentonite collected from Gampo40 mine located in South Korea may be pulverized to a size of about 2 mm or smaller, and, then, the fine particles may be dissolved in the aqua regia.

The aqua regia may be a mixture of hydrochloric acid (HCl) and nitric acid ($HNO_3$) at a molar ratio of about 1:3. For example, the aqua regia may be produced by mixing approximately 35% to 40% concentrated hydrochloric acid aqueous solution with approximately 60% to 70% concentrated nitric acid aqueous solution.

In order to completely dissolve the bentonite fine particles, the bentonite fine particles may be added to the aqua regia and then stirred for about 3 to 5 hours.

Generally, bentonite is not soluble in hydrochloric acid alone or in nitric acid alone. The present inventors have confirmed from various experiments that the bentonite is completely dissolved in the aqua regia as described above.

In the second step (S120), the sodium hydroxide may be added in the form of an aqueous solution to the aqua regia solution in which the bentonite has been dissolved.

In one embodiment, to produce the mixed solution, an aqueous sodium hydroxide solution at a concentration of about 3 to 7 M may be added to the aqua regia solution in which the bentonite has been dissolved such that pH of the mixed solution is in the range of about 11 to 13.

When the pH of the mixed solution is smaller than 11 or greater than 13, a phase of the synthesized montmorillonite may be uneven, the yield of montmorillonite may be lowered, and other species minerals may be synthesized.

When the concentration of the sodium hydroxide aqueous solution is smaller than 3 M, montmorillonite may not be synthesized. When the concentration of the sodium hydroxide aqueous solution exceeds 7 M, cancrinite may be synthesized rather than montmorillonite. Preferably, the aqueous sodium hydroxide solution of a concentration of about 3 to 5 M may be added to the aqua regia solution in which the bentonite has been dissolved.

In this connection, the concentration of the aqueous sodium hydroxide solution greatly affects the properties of the material produced in the hydrothermal synthesis reaction. For example, when a low concentration sodium hydroxide solution is added, the amount of water to be added is increased in order to satisfy the pH condition of the mixed solution. When a high concentration of sodium hydroxide solution is added, the amount of water to be added is reduced to satisfy the pH condition of the mixed solution. This change in the amount of water changes the amount of saturated water vapor generated during the hydrothermal synthesis process and thus has a great influence on the properties of the material to be synthesized. Thus, according to the present disclosure, about 3 to 7 M aqueous sodium hydroxide solution may be added to synthesize high purity montmorillonite.

In one embodiment, the sodium hydroxide aqueous solution may be added at room temperature to the aqua regia solution in which bentonite has been dissolved. Then, this mixed solution may be stirred for about 3 to 5 hours.

In the third step S130, in order to hydrothermally synthesize the montmorillonite crystals, the mixed solution may be maintained in a sealed state at a temperature of about 90° C. inclusive to 100° C. exclusive for about 20 to 30 hours. In this case, the amount of saturated water vapor inside a vessel for sealing the mixed solution therein may be in a range of about 421.5 $g/m^3$ inclusive to about 594.5 $g/m^3$ inclusive. Further, a saturated water vapor pressure in the vessel may be in a range of about 705.29 hPa inclusive to about 1022.31 hPa inclusive. The amount of saturated water vapor and the saturated water vapor pressure in the vessel are greatly influenced by the concentration of the aqueous sodium hydroxide solution added as described above.

In one embodiment, a structural derivative compound may be further added to improve crystallinity and purity of montmorillonite synthesized from the mixed solution.

The montmorillonite produced according to the present disclosure may have a specific surface area of about 125 to 135 $cm^2/g$. These values are significantly larger than the specific surface area 105.346 $cm^2/g$ of montmorillonite as produced by a conventional wet refining method via gravity settling and magnetic based separation of the natural bentonite. Therefore, montmorillonite produced according to the present disclosure is more suitable as a source material for pharmaceuticals or a raw material for cosmetics.

According to the present disclosure, the relatively low-temperature hydrothermal synthesis using the readily available natural bentonite as a starting material may allow synthesizing montmorillonite with high purity and high specific surface area.

Hereinafter, the present examples and comparative examples of the present disclosure, and experimental examples thereof will be described in detail. However, the following present examples are merely some embodiments of the present disclosure. The present disclosure should not be construed as limited to the present examples.

The Present Example 1

3 g of bentonite powders, each powder having a size of 1 mm or smaller was dissolved in 20 mL of aqua regia. At this time, the bentonite powder is obtained as follows: calcium type bentonite collected from the Gampo40 mine located in Gyeongju, Korea was pulverized and then powders having a size smaller than or equal to 1 mm (No. 18 sieve or 16 mesh) were selected. As the aqua regia, a mixture of hydrochloric acid and nitric acid in a volume ratio of 3:1 was used. The selected bentonite powders were added to the aqua regia and stirred for 4 hours to completely dissolve the bentonite powders.

To the aqua regia solution in which the bentonite powder was dissolved, 50 mL of sodium hydroxide (NaOH) solution with concentration of 4M was added, followed by stirring at room temperature for 4 hours to produce a mixed solution. The pH of the mixed solution was measured to be 12.3.

Then, the mixed solution was sealed in a hydrothermal synthesis vessel, which, in turn, is kept in an oven at 95° C. for 24 hours.

The Present Example 2

With the exception of the following difference, the hydrothermal synthesis process was carried out in the same way as the present example 1: A mixed solution of pH 12.72 as produced by adding 50 mL of sodium hydroxide (NaOH) solution having a concentration of 6M was added to aqua regia solution in which bentonite powder was dissolved.

The Comparative Example 1

Except for the following difference, the hydrothermal synthesis process was carried out in the same way as the present example 1: a solution of aqua regia in which bentonite powder was dissolved without sodium hydroxide (NaOH) solution added thereto was used as a solution for synthesis. At this time, the pH of the aqua regia solution into which the sodium hydroxide (NaOH) solution was not added and the bentonite powder was dissolved was 0.45.

The Comparative Example 2

Except for the following difference, the hydrothermal synthesis process was carried out in the same way as the present example 1: a mixed solution of pH 0.47 was prepared by adding 50 mL of sodium hydroxide (NaOH) solution having a concentration of 2M to aqua regia solution in which bentonite powder was dissolved.

The Comparative Example 3

Except for the following difference, the hydrothermal synthesis process was carried out in the same way as the present example 1: a mixed solution of pH 12.69 as produced by adding 50 mL of 8M NaOH aqueous solution to aqua regia solution in which bentonite powder was dissolved was used.

The Comparative Example 4

Hydrothermal synthesis was carried out in the same manner as the present example 1, except that a synthetic solution of pH 12.54 was used which was produced by adding 50 mL of sodium hydroxide (NaOH) solution at a concentration of 10M to aqua regia solution in which bentonite powder was dissolved.

The Comparative Example 5

Hydrothermal synthesis was carried out in the same manner as in the present example 1, except that a synthetic solution of pH 12.35 was used which was produced by adding 50 mL of a 12M sodium hydroxide (NaOH) solution to aqua regia solution in which bentonite powder was dissolved.

Experimental Example

Table 1 shows the experimental results according to the present examples 1 and 2 and the comparative examples 1 to 5. FIG. 2 is an X-ray diffraction pattern measured for calcium-type bentonite taken from Gampo40 mine (located in South Korea) as a starting material. FIG. 3 to FIG. 9 are X-ray diffraction patterns measured for materials synthesized according to the present examples 1 and 2 and comparative examples 1 to 5. The X-ray diffraction patterns of FIGS. 3 to 9 were measured after the synthesized precipitated material was washed multiple times with distilled water and dried in an oven at 60 degrees C. for one day.

TABLE 1

|  | Comparative example 1 (0 M) | Comparative example 2 (2 M) | Present example 1 (4 M) | Present example 2 (6 M) | Comparative example 3 (8 M) | Comparative example 4 (10 M) | Comparative example 5 (12 M) |
|---|---|---|---|---|---|---|---|
| pH | 0.45 | 0.47 | 12.30 | 12.72 | 12.69 | 12.54 | 12.35 |
| Layer separation | Occurrence | Occurrence | non-occurrence | non-occurrence | Occurrence | Occurrence | Occurrence |
| Supernatant | light yellow | light yellow | — | — | light brown | light brown | light brown |
| Precipitate | light brown | light brown | light brown | light brown | light brown | light brown | light brown |

Referring to FIG. 3 together with Table 1 and FIG. 2, the intensity of the characteristic main (001) peak of montmorillonite as produced via the present example is found to be higher compared with the calcium type bentonite obtained from Gampo No. 40 mine, which is the starting material. It may be confirmed that peaks of zeolite (heulandite) and feldspar, which are considered to be impurities, are relatively reduced or disappear. It may be confirmed that the purity of the synthesized montmorillonite is improved. However, it is confirmed that crystalline quartz is not dissolved in aqua regia and is included in the synthesized material.

Referring to FIG. 4, with reference to Table 1, in the comparative examples, the peak of montmorillonite is reduced and the peak of cancrinite is increased, compared to the present example 1. Thus, it may be seen that a relatively large number of montmorillonites were synthesized in the present example 1, compared to the comparative examples.

Referring to FIG. 5 and FIG. 6 together with Table 1, it may be confirmed that montmorillonite is not synthesized when synthesizing was performed according to the comparative examples 1 and 2. This is because the pH of the mixed solution is low.

Referring to FIGS. 7 to 9 together with Table 1, although the pH of the mixed solution is very similar to that of the present example 1, montmorillonite is almost not synthesized, and most of the cancrinite is synthesized. This is due to the decrease of the saturated water vapor amount and the saturated water vapor pressure in the hydrothermal synthesis vessel due to the addition of the high concentration sodium hydroxide solution.

The specific surface area of montmorillonite as synthesized according to the present example 1 was measured to be about 129.420 m$^2$/g.

What is claimed is:

1. A method for synthesizing montmorillonite, the method comprising:
   dissolving bentonite in aqua regia to produce a first solution;
   adding sodium hydroxide (NaOH) to the first solution to produce a mixed solution; and
   maintaining the mixed solution at a temperature of 90° C. inclusive to 100° C. exclusive to synthesize montmorillonite crystals,
   wherein adding the sodium hydroxide (NaOH) to the first solution includes adding to the first solution a sodium hydroxide aqueous solution having a concentration of 3 M to 7 M and
   wherein the sodium hydroxide aqueous solution is added to the first solution so that pH of the mixed solution is in a range of 11 to 13.

2. The method of claim 1, wherein the bentonite includes finely-pulverized particles made of natural bentonite, each particle having a size of 2 mm or smaller,
   wherein the aqua regia includes a mixture of hydrochloric acid (HCl) and nitric acid (HNO$_3$) at a molar ratio of about 1:3.

3. The method of claim 1, wherein maintaining the mixed solution includes maintaining the mixed solution in a sealed state for about 20 to 30 hours.

4. The method of claim 1, wherein the synthesized montmorillonite crystals have a specific surface area of about 125 to 135 cm$^2$/g.

* * * * *